US005728904A

United States Patent [19]

Van Der Puy et al.

[11] Patent Number: 5,728,904
[45] Date of Patent: Mar. 17, 1998

[54] PROCESS FOR THE PREPARATION OF 1,1,1, 3,3-PENTAFLUOROPROPANE

[75] Inventors: Michael Van Der Puy; Richard E. Eibeck; Lois A. S. Ellis; G. V. Bindu Madhavan, all of Erie, N.Y.

[73] Assignee: AlliedSignal Inc., Morristown, N.J.

[21] Appl. No.: 679,938

[22] Filed: Jul. 15, 1996

Related U.S. Application Data

[63] Continuation of Ser. No. 361,005, Dec. 21, 1994, abandoned, which is a continuation of Ser. No. 099,676, Jul. 29, 1993, abandoned.

[51] Int. Cl.$^6$ ............................. C07C 19/08; C07C 17/08
[52] U.S. Cl. ........................... 570/176; 570/166; 570/168
[58] Field of Search ................................ 570/257, 176, 570/168, 188

[56] References Cited

U.S. PATENT DOCUMENTS

| | | | |
|---|---|---|---|
| 2,560,838 | 7/1951 | Arnold | 260/653 |
| 2,942,036 | 6/1960 | Smith et al. | 260/653 |
| 3,651,019 | 3/1972 | Asscher et al. | 260/77.2 |
| 5,202,509 | 4/1993 | Laviron et al. | 570/168 |
| 5,347,059 | 9/1994 | Pennetreau et al. | 570/166 |

FOREIGN PATENT DOCUMENTS

| | | | |
|---|---|---|---|
| 684687 | 4/1964 | Canada | 570/176 |
| 0 539 989 | 10/1992 | European Pat. Off. . | |
| 0 522 638 | 4/1993 | European Pat. Off. . | |
| 0 522 639 | 4/1993 | European Pat. Off. . | |
| 1418930 | 10/1968 | Germany | 570/257 |
| 1146463 | 3/1969 | United Kingdom | 570/257 |

OTHER PUBLICATIONS

Chem. Abstr., (1991), 114: 125031q, p. 125026.
Chem. Abstr., (1961), 55, p. 349f.
Burdon et al., "Partial Fluorination of Tetrahydrofuran with Cobalt Trifluoride", J. Chem. Soc., C, (1969), p. 1739.
Asscher, et al., "Chlorine Activation by Redox–transfer . . . ", J. Chem. Soc., (1961), p. 2261.

*Primary Examiner*—Alan Siegel
*Attorney, Agent, or Firm*—Jay P. Friedenson

[57] ABSTRACT

This invention is related to the preparation of hydrofluorocarbons (HFCs). Specifically, it relates to the manufacture of 1,1,1,3,3-pentafluoropropane, $CF_3CH_2CF_2H$ (HFC-245fa) by the steps comprising (1) the formation of $CCl_3CH_2CCl_3$ by the reaction of $CCl_4$ with vinylidene chloride; (2) the conversion of $CCl_3CH_2CCl_3$ to $CF_3CH_2CF_2Cl$ by reaction with HF in the presence of a fluorination catalyst, selected from $TiCl_4$, $SnCl_4$ or mixtures thereof; and (3) reduction of $CF_3CH_2CF_2Cl$ to $CF_3CH_2CF_2H$.

12 Claims, No Drawings

PROCESS FOR THE PREPARATION OF 1,1,1,3,3-PENTAFLUOROPROPANE

This application is a continuation of application Ser. No. 08/361,005 filed Dec. 21, 1994 now abandoned which is a continuation of application Ser. No. 08/099,676 filed Jul. 29, 1993 now abandoned.

BACKGROUND OF INVENTION

This invention is related to the preparation of hydrofluorocarbons (HFCs). Specifically, it relates to the manufacture of 1,1,1,3,3-pentafluoropropane, $CF_3CH_2CF_2H$, which is referred to in the art as HFC-245fa.

HFCs are of current interest due to their potential to replace ozone depleting CFCs and HCFCs which are used in a variety of applications including refrigerants, propellants, blowing agents, and solvents. The compound $CF_3CH_2CF_2H$ has physical properties, including a boiling point of about 14° C., which makes it particularly attractive as a blowing agent or propellant. Its ability to function in a manner similar to CFC-11 ($CCl_3F$, bp 24° C.), a well known aerosol propellant at the time, was noted by Smith and Woolf in U.S. Pat. No. 2,942,036 (1960). Ger. Offen. DE 3,903,336, 1990 (EP 381 986 A) also states (using a generic formula) that $CF_3CH_2CF_2H$ may be used as a propellant or blowing agent. The use of HFC-245fa as a heat transfer agent is also mentioned in Jpn. Kokai Tokyo Koho JP 02,272,086 (Chem. Abstr. 1991, 114, 125031q).

1,1,1,3,3-Pentafluoropropane was first made by the reduction of $CF_3CCl_2CF_2Cl$ over a palladium catalyst (Smith and Woolf, U.S. Pat. No. 2,942,036, 1960). Materials exiting the reaction zone including $CF_3CH_2CHF_2$, $CF_3CH=CF_2$, $CF_3CCl=CF_2$, and unreacted starting material. The desired $CF_3CF_2CF_2H$ was formed in yields up to about 60%, but the source of the starting material was not disclosed. Reduction of 1,1,1,3,3-pentafluoropropene was disclosed by Knunyants et al. (Chem. Abstr., 1961, 55, 349f). The yield of pentafluoropropane was 70%. The only other preparation of $CF_3CF_2CF_2H$ we are aware of, is its formation, in low yield, during the elemental fluorination of tetrahydrofuran (Burdon et al., J. Chem. Soc., C, 1969, 1739).

It is the object of this invention to provide a means of manufacturing 1,1,1,3,3-pentafluoropropane which is economical and amenable to large scale, using readily available raw materials. The process of this invention involves three basic steps, of which any step or combination thereof is novel in the art.

The three steps of the process of this invention are as follows:

1) the formation of $CCl_3CH_2CCl_3$ by the reaction of $CCl_4$ with vinylidene chloride;

2) the conversion of $CCl_3CH_2CCl_3$ to $CF_3CH_2CF_2Cl$ by reaction with HF in the presence of a fluorination catalyst, selected from $TiCl_4$, $SnCl_4$ or mixtures thereof; and 3) reduction of $CF_3CH_2CF_2Cl$ to $CF_3CH_2CF_2H$.

Each step is conducted under process conditions, i.e. temperature and pressure, sufficient to produce te desired product as discussed herein.

DETAILED DESCRIPTION

The telomerization of vinylidene chloride by reaction with $CCl_4$ is known in the art and has been studied in some detail. The telomerization reaction produces compounds of the formula $CCl_3(CH_2Cl)_nCl$, where n varies as needed for the products desired. The telomerization of vinylidene chloride can be initiated by several means, but initiation with metal salts, particularly of copper, has distinct advantages for the process of this invention. The copper salts are believed to initiate the reaction by first reacting with $CCl_4$ to produce a trichloromethyl radical which then combines with vinylidene chloride, initiating the telomerization (see for example, Assher and Vofsi, J. Chem. Soc., 1961, 2261 for a discussion of the mechanism). The copper salts also terminate the telomerization by chlorine atom transfer to the growing radical chain. Thus, the chain lengths are shortened considerably, compared to e.g. peroxide initiated telomerizations. For the reactions of interest here, telomers having 3 to 9 carbon atoms are obtained in execellent yield. Some control of the telomer distribution is feasible by controlling the reaction conditions, notably the ratio of $CCl_4$ to vinylidene chloride and the type of copper salt used (see for example Belbachir et al., Makromol. Chem. 1984, 185, 1583–1595). Thus it is possible to obtain $CCl_3CH_2CCl_3$ with very little higher molecular weight telomers (see Example 1).

A variety of catalysts have been used in telomerization processes. To a large degree, many of these telomerization catalysts, including mixtures thereof, can be equivalent, and the choice of catalyst depends on cost, availability, and solubility in the reaction medium. For the telomerization reaction of this invention, it was discovered that salts of copper and iron are preferred. Overall, for the reaction of interest here, the more preferred catalysts are cuprous chloride, cupric chloride, or mixtures of the two or cuprous iodide. The amount of catalysts used in the telomerization reaction is at least about 0.1 mmol, and preferably, about 0.1 to about 50 mmol, per mole of saturated halogenated hydrocarbon (e.g., $CCl_4$ or $CCl_3CH_2CCl_3$) used. At very low concentrations, the reaction rate may be unacceptably slow, and very high catalyst concentrations may be wasteful due to the fact that the solubility limit may have been reached at even lower catalyst to $CCl_4$ ratios. Consequently, the more preferred amount of catalyst is about 1 to 20 mmol, per mole of saturated halogenated hydrocarbon.

It is also noted that a co-catalyst can be used in the telomerization process. Amines may be employed as co-catalysts, preferably in concentration of 1 to 10 moles per mole of metal catalyst (i.e. copper salt). Such amine co-catalysts include alkanol amines, alkyl amines and aromatic amines, for example ethanolamine, butyl amine, propyl amine, benzylamine, pyridine and the like.

The ratio of $CCl_4$ to vinylidene reactant will substantially alter the degree of polymerization ,i.e. average value of n for compounds of the formula $CCl_3(CH_2Cl)_nCl$. Thus, for example, if the desired product has only one more —$CH_2CCl_2$— unit than the starting material, the ratio of $CCl_4$ (or $CCl_3CH_2CCl_3$) to vinylidene chloride should be relatively high (at least about 2, and preferably, about 2 to 5), so that higher molecular weight telomers are minimized. If the desired product has two or more —$CH_2CCl_2$— units than the starting material (e.g. $CCl_3 (CH_2CCl_2)_2Cl$ from $CCl_4$), smaller ratios of $CCl_4$ to vinylidene chloride (about 0.3 to 1) should be used. The same rationale is used for a system employing vinylidene fluoride.

Useful temperatures for the telomerization reaction range from about 25° to about 225° C., preferably 80° to about 170° C., so that, depending on reactant concentrations and catalyst activity, convenient reaction times will vary from a few hours to about one day. More preferred temperatures are in the 125° to 140° C. range.

Finally a variety of solvents can be used. Any solvent which is inert to the reactants and the desired product can be used. Illustrative of such are acetonitrile, dimethylsulfoxide, dimethylformamide, tetrahydrofuran isopropanol, and tertiary butanol. We prefer acetonitrile due to its low cost, stability, easy recovery via distillation, and ability to dissolve sufficient amounts of inorganic catalyst salts. Primarily for the latter consideration, the amount of solvent is preferably from about one fourth to two thirds of the total volume, and more preferably one third to one half of the total volume. Otherwise, the amount of dissolved catalyst may be relatively low, or the output of product per run will be adversely affected due to a dilution effect.

In the second step, $CCl_3CH_2CCl_3$ is fluorinated to provide $CF_3CH_2CF_2Cl$. Previously, $CF_3CH_2CF_2Cl$ has been prepared, along with $CF_2ClCH_2CF_2Cl$, by fluorination of $CCl_3CH_2CF_2Cl$ with antimony halides (Chem. Abstr., 1981, 94: 174184u). This method, however, is unsuitable for large scale manufacture due to the cost of the fluorinating agent. The preparation of $CF_3CH_2CF_2Cl$ by the $BF_3$-catalysted addition of HF to $CF_3CH=CFCl$ is also known (R. C. Arnold, U.S. Pat. No. 2,560,838; 1951), but the source of $CF_3CH=CFCl$ was not disclosed. We have also found that HF alone or gave relatively low yields of the desired $CF_3CH_2CF_2Cl$.

Surprisingly, fluorination (of $CCl_3$ $C_2H_2$ $CCl_3$) with HF is the presence of either $TiCl_4$, or $SnCl_4$ as catalysts can provide the desired $CF_3CH_2CF_2Cl$ in synthetically useful yield. Due to the temperature required for this reaction about (75° to 175° C., and, more preferrably, 115° to 135° C.,) the reactions are conducted under pressure. The pressure may be controlled by release of by-product HCl, during the reaction process in order to provide a margin of safety if needed depending on the limitations of the equipment being used. We have found it convenient to operate at pressures of about 150 to 500 psig. The upperlimit for pressure is generally a limitation of the available equipment. The reactor consisted of a stirred autoclave fitted with a packed column attached to a condenser maintained at 0° to −20° C. Excess pressure (HCl) is vented through a valve at the top of the condenser into a scrubber. At the end of the heating period, the product and remaining HF are vented through a valve on the autoclave head, which in turn is connected to an acid scrubber and cold traps to collect the product. Under fluorinated materials, such as $CF_2ClCH_2CF_2Cl$ may be recycled along with $CCl_3CH_2CCl_3$ in subsequent batch runs.

While both $TiCl_4$ and $SnCl_4$ gave similar yields of the desired $CF_3CH_2CF_2Cl$, $TiCl_4$ is preferred due to its lower cost, lower toxicity, and availability in bulk.

The mole ratio of HF to organic should be about 4/1 to about 20/1, preferably 5/1 to about 9/1. Since overfluorinated material, $CF_3CH_2CF_3$ is generally not desired, it is more advantageous to allow more under-fluorinated material (which can be recycled) in the crude product. Overfluorinated product is keep low by smaller HF/organic ratios and lower reaction temperatures. The reaction temperatures range from 75° to about 150° C., while the preferred temperatures range from about 115° to about 135° C. Under these conditions, the reaction times range from about one to about 25 hours, and can be monitored by the rate of pressure (HCl) increase.

In the last step, $CF_3CH_2CF_2Cl$ is reduced to 1,1,1,3,3-pentafluoropropane, which is unknown in the art. The reduction can be conveniently accomplished in a continuous flow system by passing vapors of $CF_3CH_2CF_2Cl$, along with hydrogen, over a catalyst.

The latter include nickel, palladium, platinum and rhodium, which are usually supported on inert materials, such as carbon or alumina. These catalysts are available commercially and generally can be obtained having 0.5 to 20% by weight of the metal on the support material. More commonly, loadings of 0.5 to 5% weight percent are employed. Examples include 1% palladium on activated carbon granules and 0.5% platinum on ⅛" alumina pellets. The more preferred catalyst is palladium due to its lower cost compared to either platinum or rhodium.

While it is most convenient to operate to atmospheric pressure, this is not required. Both subatmospheric pressures or pressures up to 100 atmospheres may be used, the latter especially in batch operations.

In the fluorination step it may be preferable to utilize a solvent, such as methanol, ethanol and acetic acid. A base may also be beneficial to neutralize the HCl produced. Any neutralizing agent can be used, e.g. sodium hydroxide, potassium hydroxide, sodium acetate and sodium carbonate.

Useful temperatures for vapor phase reductions range from about 100° to 350° C., more preferred ranges are 150° to 250° C.

Based on reaction stoichiometry, the required ratio of hydrogen to organic is 1 mole of organic is 1 mole of hydrogen per mole of organic. From 1 to about 50 times the stoichiometric ratio may be used. A ratio of 2 to 30 times the stoichiometric amounts can be used with satisfactory results.

The most desirable conditions for the reduction will vary and will depend, in part, on the activity of the catalyst (which depends on the type of metal used, its concentration on the support material, and the nature of the support material), and the contact or residence time in the reactor. Residence times may be adjusted by changing the reaction temperature, the catalyst volume, and the flow rates of hydrogen and/or organic material to be reduced. Useful contact times range from about 0.1 sec to about 2 minutes. In the present case, more preferred contact times range from about 10 to 40 seconds at 200°–225° C. and atmospheric pressure.

In the reduction of $CF_3CH_2CF_2Cl$ at atmospheric pressure and at temperatures of about 100° to 325° C., both $CF_3CH_2CF_2H$ and $CF_3CH_2CF_2Cl$ are generally present in the reactor effluent stream. The ratio of $CF_3CH_2CF_2H$ to $CF_3CH_2CF_2Cl$ increases with increasing reaction temperature. Continuous operation at high temperatures (>250° C.) is not very advantageous, due to potential gradual loss of the original catalyst activity. Consequently, the preferred method to achieve relatively high conversions of $CF_3CH_2CF_2Cl$ to $CF_3CH_2CF_2H$ is to increase the contact time, or equivalently, to recycle the product stream until the desired conversion is obtained. After separating the desired $CF_3CH_2CF_2H$ from $CF_3CH_2CF_2Cl$, the $CF_3CH_2CF_2Cl$ may be fed into the reactor again.

EXAMPLE 1

Preparation of $CCl_3CH_2CCl_3$

A teflon-lined, magnetically stirred autoclave (575 mL capacity) was charged with 150 mL $CCl_4$, 150 mL $CH_3CN$, 0.51 g CuCl and 0.51 g $CuCl_2$ dihydrate. The autoclave was closed and evacuated briefly. Vinylidene chloride (57.7 g, 0.595 mol) was added via syringe and a rubber septum over a ball valve on the autoclave. The autoclave was then pressurized with nitrogen to 20 psig at room temperature. The mixture was heated over 1.75 h to 150° C and maintained at 150° C. for 2 h. The stirrer speed was maintained at 350 rpm. After cooling the autoclave and contents to about 15° C., the contents were removed, diluted with 400 mL water, and the organic layer separated. The aqueous layer was extracted with 50 mL methylene chloride, and the combined organic layers washed with 100 mL brine. After drying (Na$_2$SO$_4$), the organic layer was concentrated by rotary evaporation to give 140.4 g crude product. Distillation at 2.7 mm Hg gave 114.3g CCl$_3$CH$_2$CCl$_3$, bp 63°–65° C. (77% yield based on vinylidene chloride added). Its purity by GC analysis was 99.97%. 1H NMR (CDCl$_3$): singlet at 4.17 δ.

EXAMPLE 2

HF Fluorination with TiCl$_4$

A 600 mL, magnetically stirred, model autoclave fitted with a condenser (maintained at −10° C.), was evacuated, cooled to about −40° C., and charged with 0.6.9 g (0.036 mol) TiCl$_4$ followed by 64 g (0.255 mol) CCl$_3$CH$_2$CCl$_3$, and 102.5 g (5 mol) HF. The temperature was increased to 120° C. and maintained at that temperature for a total of 22 h. During the heating period, pressure in excess of 400 psig was periodically vented to an aqueous KOH scrubber which was attached to two −78° C. cold traps. At the end of the heating period, the remainder of the autoclave contents were slowly vented. The cold traps contained 36.1 g material which by GC analysis, contained 14.5% CF$_3$CH$_2$CF$_3$ and 84.0% CF$_3$CH$_2$CF$_2$Cl, corresponding to a yield for CF$_3$CH$_2$CF$_2$Cl of 69%.

EXAMPLE 3

HF Fluorination with SnCl$_4$

In the manner and apparatus described in Example 2, 63.5 g CCl$_3$CH$_2$CCl$_3$, 101.4 g HF, and 13.5 g (0.052 mol) SnCl$_4$ were heated to 125° C. for 23.5 h. The cold trap contained 41.5 g material, which by GC analysis contained 13.4% CF$_3$CH$_2$CF$_3$, 66.3% CF$_3$CH$_2$CF$_2$Cl, and 20.3% CF$_3$CH$_2$CFCl$_2$, corresponding to a yield for CF$_3$CH$_2$CF$_2$Cl of 65%. The crude products from Examples 3 and 4 were combined and distilled to give 99.4% pure (GC) CF$_3$CH$_2$CF$_2$Cl, bp 27°–30° C. 1H NMR (CDCl$_3$): δ3.2 tq (J=9 and 12 Hz).

EXAMPLE 4

Reduction of CF$_3$CH$_2$CF$_2$Cl —at 200° C.

The reactor used in this Example consisted of an electrically heated glass column containing a catalyst bed comprised of a mixture of 10 cc 1% Pd on activated carbon (4–8 mesh) and 15 cc glass helices. Hydrogen was passed over the catalyst at 140 cc/min and CF$_3$CH$_2$CF$_2$Cl was introduced at a rate of 2.25 g/h. The reaction temperature was 200° C. The material exiting the reactor was collected in a cold trap and consisted of approximately ⅓ CF$_3$CH$_2$CF$_2$H and ⅔ unreacted CF$_3$CH$_2$CF$_2$Cl by GC analysis.

EXAMPLE 5

Reduction of CF$_3$CH$_2$CF$_2$Cl at 225° C.

Example 4 was repeated, except that the reaction temperature was increased to 225° C. The volatile material which collected in the cold trap consisted, by GC analysis, of 51% CF$_3$CH$_2$CF$_2$H. The remainder was primarily unreacted CF$_3$CH$_2$CF$_2$Cl. Distillation gave CF$_3$CH$_2$CF$_2$H, bp 14° C. the recovered CF$_3$CH$_2$CF$_2$Cl was recycled to provide additional CF$_3$CH$_2$CF$_2$H.

EXAMPLE 6

Reduction of CF$_3$CH$_2$CF$_2$Cl at room temperature

An autoclave was charged with a solution of 10 g KOH in 60 mL methanol, 0.5 g 1% Pd on carbon, and 25 g (0.15 mol) CF$_3$CH$_2$CF$_2$Cl. Stirring was begun and the autoclave pressurized to 250 psig with hydrogen. After 20 hours, the contents were cooled to 0° C. and excess hydrogen was bled off. The remaining volatile organic material was then transferred to a cold receiver under vacuum. Distillation of the crude material so obtained gave CF$_3$CH$_2$CHF$_2$.

What is claimed is:

1. A process for the preparation of 1,1,1,3,3-pentafluoropropane (CF$_3$CH$_2$CF$_2$H) comprising the steps of:
   a) reacting CCl$_3$CH$_2$CCl$_3$ with HF in the presence of a catalyst selected from the group consisting of tetravalent tin and tetravalent titanium, in a fluorination reaction step, to produce CF$_3$CH$_2$CF$_2$Cl; and
   b) reacting said CF$_3$CH$_2$CF$_2$Cl with hydrogen, in the presence of a heterogeneous hydrogenation catalyst, in a reduction step to produce said 1,1,1,3,3-pentafluoropropane.

2. A process for the preparation of 1,1,1,3,3-pentafluoropropane in accordance with claim 1, wherein said heterogeneous hydrogenation catalyst is palladium on carbon.

3. A process for the preparation of 1,1,1,3,3-pentafluoropropane in accordance with claim 1; wherein a molar ratio of HF to CCl$_3$CH$_2$CCl$_3$ ranges from 4.0 to 20.0.

4. A process for the preparation of 1,1,1,3,3-pentafluoropropane in accordance with claim 1, wherein a molar ratio of HF to CCl$_3$CH$_2$CCl$_3$ ranges from 5.0 to 9.0.

5. A process for the preparation of 1,1,1,3,3-pentafluoropropane in accordance with claim 1, wherein said fluorination reaction step has a temperature ranging from 75° C. to 150° C.

6. A process for the preparation of 1,1,1,3,3-pentafluoropropane in accordance with claim 1, wherein said fluorination reaction step has a temperature ranging from 115° C. to 135° C.

7. A process for the preparation of 1,1,1,3,3-pentafluoropropane in accordance with claim 1, wherein said reduction step has a temperature ranging from 100° C. to 350° C.

8. A process for the preparation of 1,1,1,3,3-pentafluoropropane in accordance with claim 1, wherein said reduction step has a temperature ranging from 200° C. to 225° C.

9. A process for the preparation of 1,1,1,3,3-pentafluoropropane in accordance with claim 1, wherein a molar ratio of hydrogen to CF$_3$CH$_2$CF$_2$Cl is 1.0.

10. A process for the preparation of 1,1,1,3,3-pentafluoropropane in accordance with claim 1, wherein said reduction step has a contact time ranging from 0.1 seconds to 2 minutes.

11. A process for the preparation, of 1,1,1,3,3-pentafluoropropane in accordance with claim 1, wherein said reduction step has a contact time ranging from 10 seconds to 40 seconds.

12. A process for the preparation of 1,1,1,3,3-pentafluoropropane comprising the steps of:
   a) reacting CCl$_3$CH$_2$CCl$_3$ with HF, wherein a molar ratio of HF to CCl$_3$CH$_2$CCl$_3$ ranges from 5.0 to 9.0, in the presence of a catalyst selected from the group consisting of tetravalent tin and tetravalent titanium, in a fluorination step of a temperature ranging from 75° C. to 150° C., to produce CF$_3$CH$_2$CF$_2$Cl; and
   b) reacting said CF$_3$CH$_2$CF$_2$Cl with hydrogen, a molar ratio of CF$_3$CH$_2$CF$_2$Cl to hydrogen being 1.0, in a reduction step, at a temperature ranging from 200° C. to 225° C. for a period of 10 to 40 seconds, to produce said 1,1,1,3,3-pentafluoropropane.

* * * * *